United States Patent
Byerly et al.

(10) Patent No.: US 11,266,788 B2
(45) Date of Patent: Mar. 8, 2022

(54) DETERMINATION OF A DOSE IN A MEDICATION DELIVERY DEVICE USING TWO MOVING ARRAYS WITH TEETH AND A SENSOR

(71) Applicant: Eli Lilly and Company, Indianapolis, IN (US)

(72) Inventors: Roy Howard Byerly, Indianapolis, IN (US); Russell Wayne Perkins, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 582 days.

(21) Appl. No.: 16/091,679

(22) PCT Filed: Apr. 12, 2017

(86) PCT No.: PCT/US2017/027157
§ 371 (c)(1),
(2) Date: Oct. 5, 2018

(87) PCT Pub. No.: WO2017/184401
PCT Pub. Date: Oct. 26, 2017

(65) Prior Publication Data
US 2019/0151559 A1    May 23, 2019

Related U.S. Application Data

(60) Provisional application No. 62/324,492, filed on Apr. 19, 2016.

(51) Int. Cl.
*A61M 5/20* (2006.01)
*A61M 5/315* (2006.01)
(Continued)

(52) U.S. Cl.
CPC .......... *A61M 5/31551* (2013.01); *A61M 5/24* (2013.01); *A61M 5/3156* (2013.01);
(Continued)

(58) Field of Classification Search
CPC ............ A61M 5/31551; A61M 5/3156; A61M 2005/2444; A61M 2205/3317; A61M 2205/50
See application file for complete search history.

(56) References Cited

U.S. PATENT DOCUMENTS 685,091 A    10/1901   Becton
1,625,035 A   4/1927   Lilly
(Continued)

FOREIGN PATENT DOCUMENTS

EP    0338806    10/1989
EP    0498737     8/1992
(Continued)

OTHER PUBLICATIONS

Patent Cooperation Treaty International Search Report and the Written Opinion of the International Searching Authority pertaining to International Application No. PCT/US2017/027157; dated Jun. 26, 2017.
(Continued)

*Primary Examiner* — Rebecca E Eisenberg
*Assistant Examiner* — Tania Ismail
(74) *Attorney, Agent, or Firm* — Arthur C. H. Shum (57) ABSTRACT

Sensing systems, devices and methods are disclosed for determining the relative movement of first and second members of a medication delivery device which are proportional to the amount of a dose set and/or delivered by operation of the medication delivery device. A sensor is coupled with the first member. A pair of targets is coupled with the second member. Each target comprises an array of
(Continued)

teeth which move through an area sensed by the sensor. The sensor thereby detects characteristic values of a sensed parameter corresponding to the combined relative positions of the first and second members. The sensing system outputs this information to a processor which determines the amount of the dose set and/or delivered. Related medication delivery devices and methods are also disclosed.

16 Claims, 4 Drawing Sheets

(51) Int. Cl.
*A61M 5/24* (2006.01)
*G01D 5/14* (2006.01)
*A61M 5/31* (2006.01)

(52) U.S. Cl.
CPC ..... *G01D 5/147* (2013.01); *A61M 2005/2444* (2013.01); *A61M 2005/3126* (2013.01); *A61M 2205/3317* (2013.01); *A61M 2205/50* (2013.01); *A61M 2205/52* (2013.01)

(56) References Cited

U.S. PATENT DOCUMENTS

| | | |
|---|---|---|
| 2,853,586 A | 9/1958 | Vercesi |
| 3,399,368 A | 8/1968 | Elliott et al. |
| 3,723,061 A | 3/1973 | Stahl |
| 4,315,252 A | 2/1982 | Tagami |
| 4,486,891 A | 12/1984 | Kimoto et al. |
| 4,529,401 A | 7/1985 | Leslie et al. |
| 4,552,055 A | 11/1985 | Foxwell |
| 4,592,745 A | 6/1986 | Rex et al. |
| 4,865,591 A | 9/1989 | Sams |
| 4,883,472 A | 11/1989 | Michel |
| 4,931,041 A | 6/1990 | Faeser |
| 5,279,586 A | 1/1994 | Balkwill |
| 5,418,362 A | 5/1995 | Lusby et al. |
| 5,509,905 A | 4/1996 | Michel |
| 5,536,249 A | 7/1996 | Castellano et al. |
| 5,569,212 A | 10/1996 | Brown |
| 5,582,598 A | 12/1996 | Chanoch |
| 5,593,390 A | 1/1997 | Castellano et al. |
| 5,626,566 A | 5/1997 | Petersen et al. |
| 5,628,309 A | 5/1997 | Brown |
| 5,674,204 A | 10/1997 | Chanoch |
| 5,688,251 A | 11/1997 | Chanoch |
| 5,691,646 A | 11/1997 | Sasaki |
| 5,704,922 A | 1/1998 | Brown |
| 5,728,074 A | 3/1998 | Castellano et al. |
| 5,743,889 A | 4/1998 | Sams |
| 5,820,602 A | 10/1998 | Kovelman et al. |
| 5,827,232 A | 10/1998 | Chanoch et al. |
| 5,920,198 A | 7/1999 | Suzuki et al. |
| 5,921,966 A | 7/1999 | Bendek et al. |
| 5,925,021 A | 7/1999 | Castellano et al. |
| 5,938,642 A | 8/1999 | Burroughs et al. |
| 5,954,700 A | 9/1999 | Kovelman |
| 5,957,896 A | 9/1999 | Bendek et al. |
| 5,961,496 A | 10/1999 | Nielsen et al. |
| 6,001,089 A | 12/1999 | Burroughs et al. |
| 6,004,297 A | 12/1999 | Steenfeldt-Jensen et al. |
| D425,990 S | 5/2000 | Gravel et al. |
| 6,068,615 A | 5/2000 | Brown et al. |
| 6,080,090 A | 6/2000 | Taylor et al. |
| 6,110,152 A | 8/2000 | Kovelman |
| 6,192,891 B1 | 2/2001 | Gravel et al. |
| 6,221,046 B1 | 4/2001 | Burroughs et al. |
| 6,221,053 B1 | 4/2001 | Walters et al. |
| 6,235,004 B1 | 5/2001 | Steenfeldt-Jensen et al. |
| 6,248,095 B1 | 6/2001 | Giambattista et al. |
| 6,277,099 B1 | 8/2001 | Strowe et al. |
| 6,302,855 B1 | 10/2001 | Lav et al. |
| 6,340,357 B1 | 1/2002 | Poulsen et al. |
| 6,482,185 B1 | 11/2002 | Hartmann |
| 6,540,672 B1 | 4/2003 | Simonsen et al. |
| 6,558,320 B1 | 5/2003 | Causey, III et al. |
| 6,585,698 B1 | 7/2003 | Packman et al. |
| 6,663,602 B2 | 12/2003 | Moller |
| 6,781,522 B2 | 8/2004 | Sleva et al. |
| 6,875,195 B2 | 4/2005 | Choi |
| 7,138,806 B2 | 11/2006 | Gafner et al. |
| 7,195,616 B2 | 3/2007 | Diller et al. |
| 7,704,238 B2 | 4/2010 | Diller et al. |
| 7,992,460 B2 | 8/2011 | Bochen et al. |
| 8,049,519 B2 | 11/2011 | Nielsen et al. |
| 8,197,449 B2 | 6/2012 | Nielsen et al. |
| 8,529,520 B2 | 9/2013 | Daniel |
| 8,556,865 B2 | 10/2013 | Krulevitch et al. |
| 8,672,899 B2 | 3/2014 | Diller et al. |
| 2001/0013774 A1 | 8/2001 | Noltemeyer et al. |
| 2002/0013522 A1 | 1/2002 | Lav et al. |
| 2002/0020654 A1 | 2/2002 | Eilersen |
| 2002/0120235 A1 | 8/2002 | Enggaard |
| 2002/0177923 A1 | 11/2002 | Steffen |
| 2003/0006209 A1 | 1/2003 | Stefen et al. |
| 2005/0182358 A1 | 8/2005 | Veit et al. |
| 2005/0182360 A1 | 8/2005 | Yeandel et al. |
| 2007/0123829 A1 | 5/2007 | Atterbury et al. |
| 2008/0140018 A1 | 6/2008 | Enggaard |
| 2009/0318865 A1 | 12/2009 | Moller et al. |
| 2010/0106098 A1 | 4/2010 | Atterbury et al. |
| 2012/0238960 A1 | 9/2012 | Smith et al. |
| 2013/0072897 A1 | 3/2013 | Day et al. |
| 2013/0310756 A1 | 11/2013 | Whalley et al. |
| 2014/0074041 A1 | 3/2014 | Pedersen et al. |
| 2014/0194829 A1 | 7/2014 | Baek et al. |
| 2014/0243750 A1 | 8/2014 | Larsen et al. |
| 2015/0018775 A1 | 1/2015 | Groeschke et al. |
| 2015/0174330 A1 | 6/2015 | Nagel et al. |
| 2015/0320934 A1 | 11/2015 | Draper et al. |
| 2015/0343152 A1 | 12/2015 | Butler et al. |
| 2016/0008552 A1 | 1/2016 | Madsen et al. |
| 2016/0136353 A1 | 5/2016 | Adams |
| 2016/0259913 A1 | 9/2016 | Yu et al. |
| 2016/0296702 A1 | 10/2016 | Rasmussen et al. |
| 2016/0378951 A1 | 12/2016 | Gofman et al. |
| 2017/0023204 A1 | 1/2017 | Takeuchi et al. |
| 2017/0128674 A1 | 5/2017 | Butler et al. |
| 2017/0189625 A1 | 7/2017 | Cirillo et al. |
| 2017/0274148 A1 | 9/2017 | Mews et al. |

FOREIGN PATENT DOCUMENTS

| | | |
|---|---|---|
| EP | 0519137 | 12/1992 |
| EP | 0581925 | 2/1994 |
| EP | 0615762 | 9/1994 |
| EP | 0778034 | 6/1997 |
| EP | 0937471 | 8/1999 |
| EP | 0937472 | 8/1999 |
| EP | 1043037 | 10/2000 |
| EP | 1074273 | 2/2001 |
| EP | 1095668 | 5/2001 |
| EP | 1240913 | 9/2002 |
| EP | 2060284 | 5/2009 |
| EP | 2468340 | 6/2012 |
| EP | 2692378 | 2/2014 |
| GB | 2309801 | 8/1997 |
| WO | 9009202 | 8/1990 |
| WO | 9619872 | 6/1996 |
| WO | 0041754 | 7/2000 |
| WO | 0077472 | 12/2000 |
| WO | 0110484 | 2/2001 |
| WO | 0156635 | 8/2001 |
| WO | 0159570 | 8/2001 |
| WO | 02064196 | 8/2002 |
| WO | 02092153 | 11/2002 |
| WO | 03009461 | 1/2003 |
| WO | 03015838 | 2/2003 |
| WO | 03005891 | 11/2003 |
| WO | 2006045525 | 5/2006 |
| WO | 2011064299 | 6/2011 |

(56) References Cited

FOREIGN PATENT DOCUMENTS

| WO | 2012004298 | 1/2012 | | |
|----|------------|--------|---|---|
| WO | 2013010893 | 1/2013 | | |
| WO | 2013098421 | 7/2013 | | |
| WO | 2014037331 | 3/2014 | | |
| WO | 2014128157 | 8/2014 | | |
| WO | WO-2014161954 A1 * | 10/2014 | ........ | A61M 5/31583 |
| WO | 2015002806 | 1/2015 | | |
| WO | 2015123688 | 8/2015 | | |
| WO | 2016180873 | 11/2016 | | |
| WO | 2017021226 | 2/2017 | | |
| WO | 2017092960 | 6/2017 | | |
| WO | 2017165207 | 9/2017 | | |
| WO | 2018031390 | 2/2018 | | |
| WO | 2018111708 | 6/2018 | | |
| WO | 2018111709 | 6/2018 | | |

OTHER PUBLICATIONS

Eli Lilly and Company, Technical Dossier for the HumaPen® Pen-Injector Family, Aug. 15, 2000, pp. 1 and 10-25 provided.
Soft Pot potentiometers https://media.digikey.com/pdf/Data%20Sheets/Spectra%20Symbol/SP%20Series%20SoftPot.pdf.
Hoffman-Krippner potentiometers http://www.hoffmann-krippner.com/potentiometers-sensotoil.hml.
State Electronics potentiometers http://www.potentiometers.com.

* cited by examiner

DETERMINATION OF A DOSE IN A MEDICATION DELIVERY DEVICE USING TWO MOVING ARRAYS WITH TEETH AND A SENSOR

CROSS-REFERENCE TO RELATED APPLICATIONS

This application is a National Stage of International Application No. PCT/US2017/027157, filed Apr. 12, 2017, which claims the benefit of and priority to U.S. provisional application No. 62/324,492, filed Apr. 19, 2016, the contents of all of which are hereby incorporated herein by reference.

BACKGROUND OF THE INVENTION

The present invention pertains to medication delivery devices, and in particular to a sensing system in a medication delivery device.

A variety of medication delivery devices, including for example pen injectors, infusion pumps and syringes, are commonly used for periodic administration of medications. It is important that the proper amount of medication be supplied at these times as the health of the patient is at stake. In many instances, failure to accurately deliver the appropriate amount of medication may have serious implications for the patient.

The administration of a proper amount of medication requires that the actual dosing by the medication delivery device be accurate. The term "dosing" as used herein refers to the two key phases of administering a dose, namely, setting the dose amount and delivering the amount of the set dose. Assuring that an accurate dose is administered requires that the medication delivery device perform properly during both of these key phases of dosing.

Medication delivery devices generally utilize mechanical systems in which various members rotate or translate relative to one another. In most instances, these relative movements between members are proportional to the dose amount set and/or delivered by operation of the device. Accordingly, the art has endeavored to provide reliable systems that accurately measure the relative movement of members of a medication delivery device in order to assess the dose set and/or delivered. Such systems may include a sensor which is coupled with a first member of the medication delivery device and detects the relative movement of sensed components coupled with a second member of the device. The prior art has described a variety of sensing systems based upon the movement of objects through a sensed area, including optical, tactile, electrical and magnetic systems.

BRIEF SUMMARY OF THE INVENTION

In one form thereof, the present invention provides a sensing system for a medication delivery device comprising a first member of the medication delivery device; a second member of the medication delivery device moveable relative to the first member in proportion to at least one of an amount of a dose set and an amount of a dose delivered by operation of the medication delivery device; a sensor coupled with the first member, the sensor being operable to detect a sensed parameter within a sensed area of the sensor; a first, passive target coupled with the second member and having an array of first teeth positioned to move through the sensed area as the second member moves relative to the first member, the first teeth being substantially identical in shape and uniformly spaced a first distance; a second, passive target coupled with the second member and having an array of second teeth positioned to move through the sensed area as the second member moves relative to the first member, the second teeth being substantially identical in shape and uniformly spaced a second distance different from the first distance, the first target being fixed against movement relative to the second target, the sensor being operable to sense a characteristic of the sensed parameter representative of a relative position between the first and second members based on the combined positions of the first and second teeth within the sensed area, and to generate an output correlated to the sensed characteristic; and a processor operably connected to the sensor to receive the output from the sensor, the processor being configured to identify the position of the first member relative to the second member based on the sensor output.

In another form thereof, the present invention provides a medication delivery device comprising: a first member of the medication delivery device; a second member of the medication delivery device moveable relative to the first member in proportion to at least one of the amount of a dose set and the amount of a dose delivered by operation of the medication delivery device; a sensor coupled with the first member, the sensor being operable to detect a sensed parameter within a sensed area of the sensor; a first, passive target coupled with the second member and having an array of first teeth positioned to move through the sensed area as the second member moves relative to the first member, the first teeth being substantially identical in shape and uniformly spaced a first distance; a second, passive target coupled with the second member and having an array of second teeth positioned to move through the sensed area as the second member moves relative to the first member, the second teeth being substantially identical in shape and uniformly spaced a second distance different from the first distance, the first target being fixed against movement relative to the second target, the sensor being operable to sense a characteristic of the sensed parameter representative of a relative position between the first and second members based on the combined positions of the first and second teeth within the sensed area, and to generate an output correlated to the sensed characteristic; and a processor operably connected to the sensor to receive the output from the sensor, the processor being configured to identify the position of the first member relative to the second member based on the sensor output.

One advantage of the present invention is that a sensing system may be provided that provides an accurate and reliable assessment of the amount of medication that has been set and/or delivered by a medication delivery device.

Another advantage of the present invention is that a sensing system may be provided that requires few individual parts, and is compact and readily adapted to a variety of medication delivery devices.

Further objects, features and embodiments of the present invention will become apparent from the detailed description and drawings provided herewith.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

For the purpose of promoting an understanding of the principles of the invention, references are made herein to examples illustrated in the drawings, and specific language is used to describe the same. It will nevertheless be understood that no limitation of the scope of the invention is thereby intended. Any alterations and further modifications in the described embodiments, and any further applications of the concepts disclosed herein, are contemplated as would normally occur to one skilled in the relevant art. Examples of these concepts are shown in detail, but it will be apparent that some features and details have been omitted for the sake of clarity.

The present invention relates generally to sensing systems for determining the amount of a dose set and/or delivered by a medication delivery device. In particular, the present invention relates to the measurement of relative movement between members of the medication delivery device. The relative movements may be typically rotational (angular), translational (linear), or a combination of both. The medication delivery device may be any device which is used to set or deliver a dose of a medication, such as pen injectors, infusion pumps and syringes. The medication may be any of a type that may be administered by such a medication delivery device.

The system includes a first member of a medication delivery device that moves relative to a second member during dose setting and/or delivery in a manner that is proportional to the amount of the set or delivered dose. The sensing system includes a sensor coupled with the first member and the combination of at least two sensed components, herein referred to as "targets", coupled with the second member.

The term "coupled" encompasses any manner of fixing the position of the sensor and the targets to the respective members of the medication delivery device. For example, the sensor and/or targets may be separate components which are directly positioned on, received within or attached to the associated members. Alternatively, there may be one or more other components which indirectly connect the sensing system components with the members. In other embodiments, the sensor and/or targets may include components, such as a sensing element or teeth, which are formed integrally with the members. It will be appreciated by those skilled in the art that it is a sufficient "coupling" of the sensing system components if the sensor and the targets are thereby caused to move in unison, or proportionally, with the first and second members as those members move relative to one another during dose setting and/or delivery.

The sensor is operable to detect a parameter within a sensed area. Each target includes an array of teeth which may be positioned within the sensed area and which as a result have an effect on the sensed parameter. In particular, the sensor and targets are coupled with the first and second members, respectively, to cause the teeth to move through the sensed area of the sensor during relative movement between the members. The term sensor refers to any device which detects a characteristic of a sensed parameter which varies in relationship to the positions of the teeth within the sensed area. The term teeth refers to any series of projections from the targets which extend into the sensed area of the sensor and which directly or indirectly affect the sensed parameter.

The sensed parameter may be anything affected by the positions of the teeth within the sensed area. The sensed parameter may, for example, be a capacitance, conductance, resistance, impedance or voltage sensed by the sensor. The sensed parameter may be detected in various manners known in the art. For example, the sensed parameter may be associated with a field, such as a magnetic field, which is imposed upon the sensed area and which is altered based upon the positions of the teeth within the field. The alterations of the field then change the sensed parameter in direct relation to the positions of the teeth in the sensed area.

In one embodiment, the sensing system includes a sensing element located within a field in a position that an attribute of the sensing element is affected by the applied field. For example, in a magneto-resistive type sensor the distortion of an applied magnetic field results in a characteristic change in the resistance of the sensing element. Similarly, Hall Effect sensors detect changes in the voltage resulting from distortions in an applied magnetic field. Each different position of the combined targets presents a unique physical profile of teeth relative to the sensed area, which has an associated effect on the sensed parameter of the sensor. The different positions of the targets therefore result in a value for the sensed parameter that is characteristic of the relative positions of the sensor and the targets.

The sensing system is thereby able to identify the positions of the teeth, and therefore also the specific positions of the targets relative to the sensor. Identifying the starting and ending positions of the targets when setting or delivering a dose provides an indication of the relative movement of the two members. Since this movement is proportional to the amount of dose that is set or delivered, the dose amounts can be determined.

The teeth perform as passive targets, meaning that they are not active components such as permanent magnets. The teeth distort the sensed parameter, rather than creating it. The targets may be constructed of any material(s) suitable for inclusion in the medication delivery device and effecting a detectable change in the sensed parameter based on the configuration of the teeth in the sensed area. Preferably, the teeth of the targets, or the entire targets, may be configured and made of a material which enhances the operation of the sensing system. For example, the use of a ferromagnetic material can significantly induce or amplify the effect of the positions of the teeth on a magnetic field.

Figure 1:
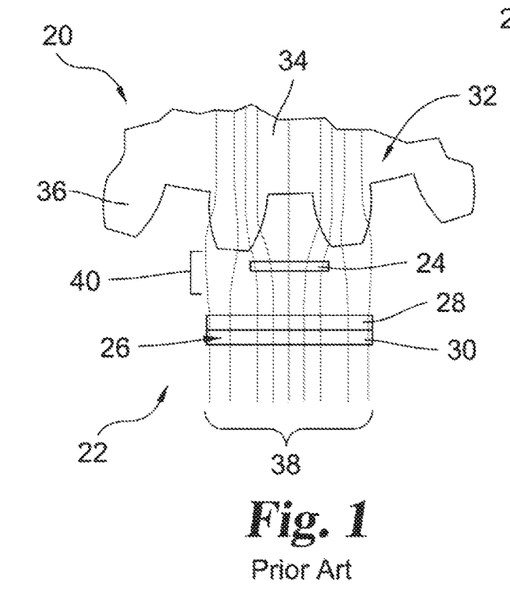
FIGS. 1 and 2 are schematic views of the prior art generally showing the sensing of a target having an array of spaced teeth.
Figure 2:
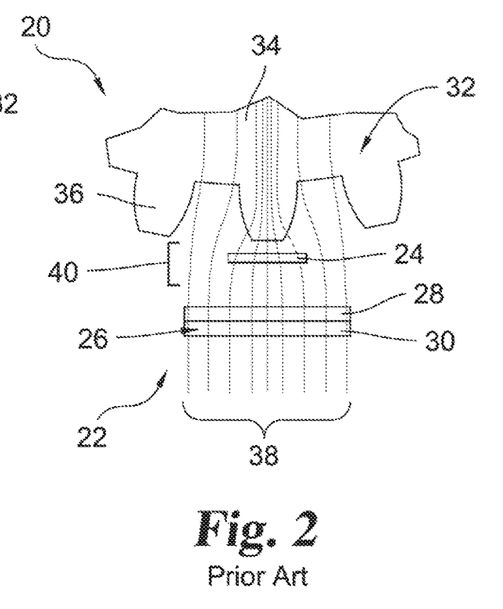

General principles involved with the sensing system are exemplified in the prior art as shown in FIGS. 1-2. Sensing system 20 comprises a magneto-resistive sensor 22 including a sensing element 24 and a magnet 26 comprising a pole 28 and an opposed pole 30. The sensing system further comprises a target 32 which includes a disc-shaped body 34 carrying a circumferential array of teeth 36. Magnet 26 creates a magnetic field represented by flux lines 38 illustrated as passing through sensing element 24, magnet 26, teeth 36, and body 34. The teeth are thereby positioned to move through a sensed area 40 of the sensor 22. Further, teeth 36 may comprise a material, such as a ferromagnetic material, to enhance the distortions in the magnetic field as represented by the pattern of magnetic flux lines 38. The differing positions of the teeth within the sensed area produce changes in the magnetic field which are detected by the sensor 22.

Each different position of teeth 36 relative to sensor 22 results in a flux pattern that is a characteristic "signature" corresponding to that position. The density, direction, and/or intensity of magnetic flux lines 38 vary as peaks and valleys of teeth 36 fall in different positions, thus changing the sensed parameter of sensing element 24. For example, comparing FIGS. 1 and 2 it is apparent that the magnetic field distortions have changed as teeth 36 assumed different positions relative to sensing element 24. These different magnetic field patterns modify, for example, the resistance measured for sensing element 24. In the example of FIGS. 1-2 only a single target is shown and all of the teeth have the same shape and are equally spaced. Consequently, the sensor does not distinguish between two different teeth located in the same position relative to the sensor.

By way of example, the following disclosure relates to a sensing system which is based on the detection of variations in an imposed magnetic field caused by two arrays of teeth. In a preferred embodiment, the sensing system utilizes a magneto-resistive sensor which assess changes to a measured resistance resulting from variations in the surrounding magnetic field. However, any sensing system based on the effect caused by movement of two arrays of teeth through the sensed area may be used. Other examples of sensors useful in the present invention are sensors which measure changes in capacitance, conductance, voltage or other properties.

The present sensing system combines at least first and second targets including arrays of spaced teeth, respectively. The two targets are coupled directly or indirectly to the same member of the medication delivery device such that there is no relative movement between the two targets and they act essentially as a single target for the sensor. In certain embodiments, the targets are attached to each other or comprise an integral unit. The relative positioning of one target to the other may be easily provided by a key or other mechanism to positively couple the targets to the medication delivery device and/or to each other.

The sensor and the targets are positioned such that both arrays of teeth pass through the sensed area of the sensor as the members of the medication delivery device move relative to one another. The teeth thereby provide a physical profile within the sensed area of a single sensor that is a combination of teeth from both targets. This "combined profile" presents a more complex and varied profile than would be caused by either target alone. For a given position of the targets, the sensor generates one output representing the combined positions of the teeth of both targets.

The first target includes an array of first teeth which preferably are substantially or completely identical in shape and are uniformly spaced. The second target includes an array of second teeth which preferably are substantially or completely identical in shape, which shape may be the same as or different from the shape of the first teeth. The teeth of the second target also are preferably uniformly spaced, but the spacing is different than for the first teeth. This use of targets having uniformly shaped and spaced teeth allows for the use of simple physical structures as the targets that are readily and inexpensively produced.

The relative spacing for the two arrays is selected to provide any of a variety of desired effects. For example, if the spacing of one set of teeth is twice that of the other, then there will be an alternating pattern for the combined profile of the teeth as presented in the sensed area. There will then also be a corresponding alternating effect on the sensed parameter. Other pairings for the spacing of the teeth result in patterns which repeat, for example, every three or four teeth.

A preferred embodiment includes positions of the first and second teeth that provide unique combined profiles of teeth throughout the expanse of teeth passing through the sensed area. This results when the spacing of the teeth on the first target is such that there is no repeat of the relative positions of the first teeth with the teeth on the second target. This will occur, for example, for circular arrays of teeth in which the second array has one more tooth than the first array. In this embodiment, the relative positions of teeth of the two targets will differ throughout the circumferences of the targets. This approach is particularly advantageous in that it provides a unique profile, and resulting signature, for each position of the targets.

The resolution of the sensing element will be affected by the closeness of the teeth. Teeth which are spaced closer together will provide a greater number of influences on the sensed parameter for a given distance of travel. For example, a circular array of thirty-two teeth would have a spacing of 11.25 degrees, whereas one with fifty teeth would have a spacing of about 7.2 degrees.

In one application of the present invention, the sensing system detects the positions of first and second members which relatively rotate about an axis. The targets preferably comprise circular arrays of outwardly-extending teeth positioned to rotate about the same axis. The two targets are positioned such that the teeth of both targets pass through the same sensed area of a single sensor. For circular arrays of teeth, this generally means that the two arrays will have a similar radius.

Figure 3:
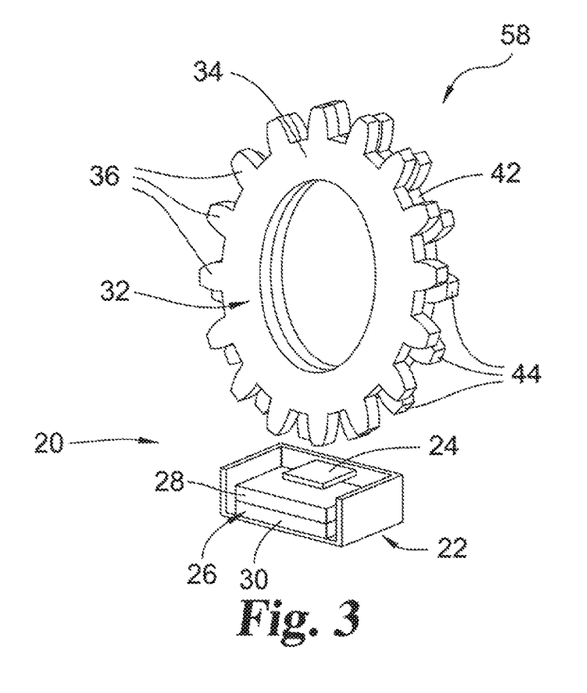
FIG. 3 is a perspective view showing an arrangement of components of a sensing system.
Figure 4:
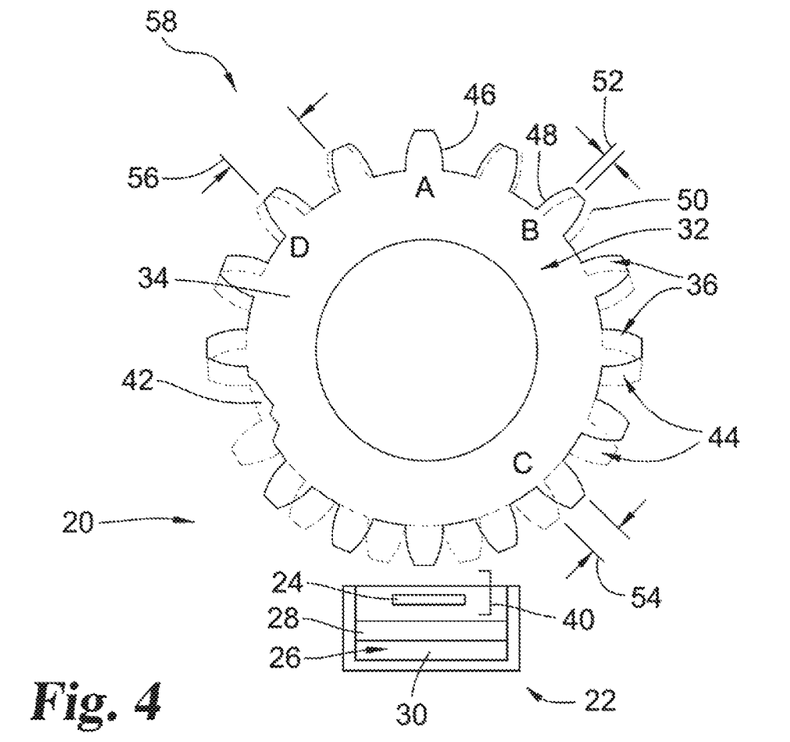
FIG. 4 is a front view of the sensing system of FIG. 3.

The "combined profiles" of teeth are demonstrated in the embodiment of FIGS. 3-4. First target 32 includes sixteen teeth 36 (solid lines) and second target 42 includes fifteen teeth 44 (dotted lines in FIG. 4). The spacing of the teeth for first target 32 is therefore smaller than the spacing of the teeth for second target 42. This difference in spacing results in varying relative positions of the teeth for one target versus the other such that a unique physical configuration of teeth occurs throughout the perimeters of the targets. For example, at position "A", tooth 46 of first target 32 is aligned with a tooth of second target 42 not visible behind tooth 46. However, at position "B" the teeth 48 and 50 are displaced by an amount 52. At positions "C" and "D" on target 32, the teeth 36 and 44 are displaced by successively larger amounts 54 and 56. It will therefore be observed that in this embodiment sensing system 58 has no relative positions of teeth 36 and 44 which are duplicated.

The effect of the teeth on the magnetic field therefore provides a different and distinctive signature for each position around the targets. This allows the sensing system 20 to specifically identify the relative position of one member of the medication delivery device relative to another with which it relatively rotates. For example, the sensing system can determine when position "A" of target 32 is within the sensed area when it detects the signature associated with this aligned position of the teeth on the two targets. The sensing system is also able to identify the relative direction of movement based on a comparison of successive, uniquely-identifiable positions of the targets relative to the sensor.

A medication delivery device is typically configured such that only discrete increments of doses can be achieved, e.g., a whole number, possibly with half amounts, of dose units. There may therefore be a known degree of angular displacement of the relatively rotating members which corresponds to one unit of dose. In accordance with the present invention, it is possible to correlate the spacing of the teeth with the movement related to setting or delivering, for example, a unit dose for the medication delivery device. For example, the spacing for a circular array of sixteen teeth is 22.5 degrees. Thus, if the medication delivery device requires a relative rotation of the first and second members of 22.5 degrees to set or deliver a unit of dose, then the use of a circular array of sixteen teeth may be selected.

Since the sensing system is able to identify different specific positions, it is able to identify start and stop positions between the first and second members during dose setting or delivery. Identifying these positions allows for the determination of the overall relative movement between the members. This in turn can be converted to the amount of the set or delivered dose. The sensing system may also determine intermediate positions and determine the extent of rotation by counting the successive movements from start to finish.

Figure 5:
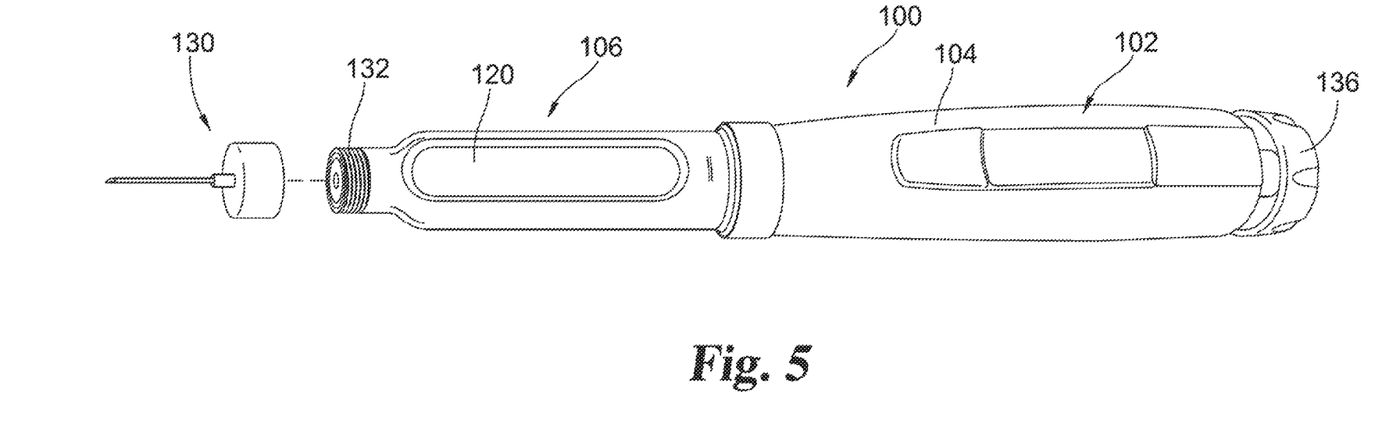
FIG. 5 is a perspective view of components of a medication delivery device including a sensing system.
Figure 6:
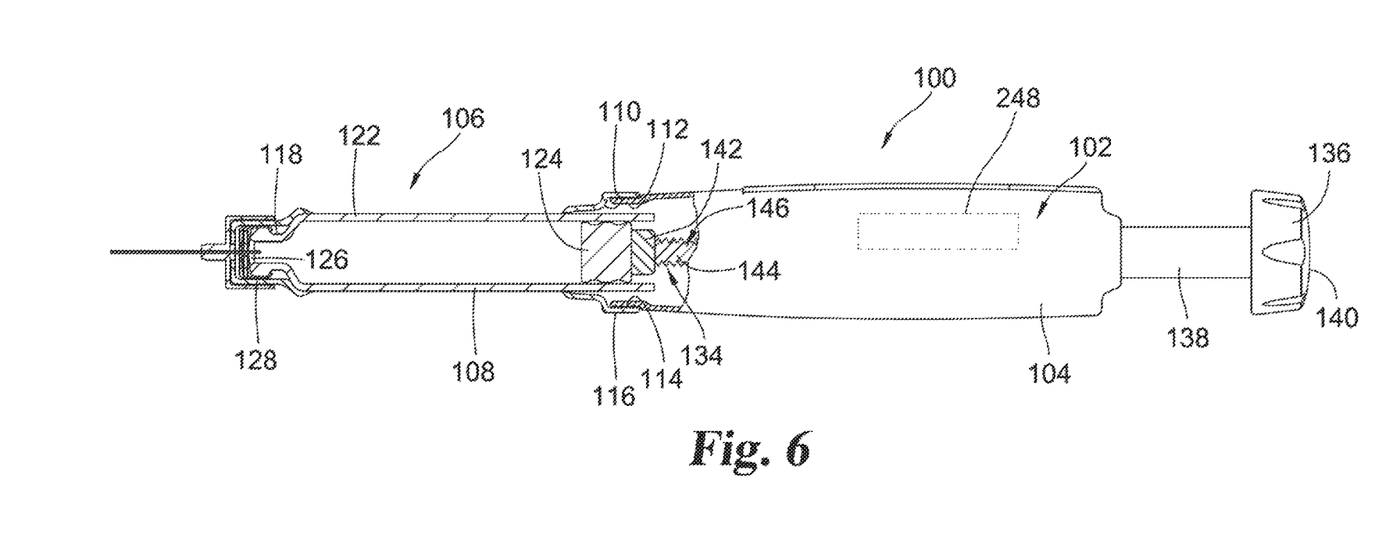
FIG. 6 is a plan view, partially in cross section, of the medication delivery device of FIG. 5.
Figure 7:
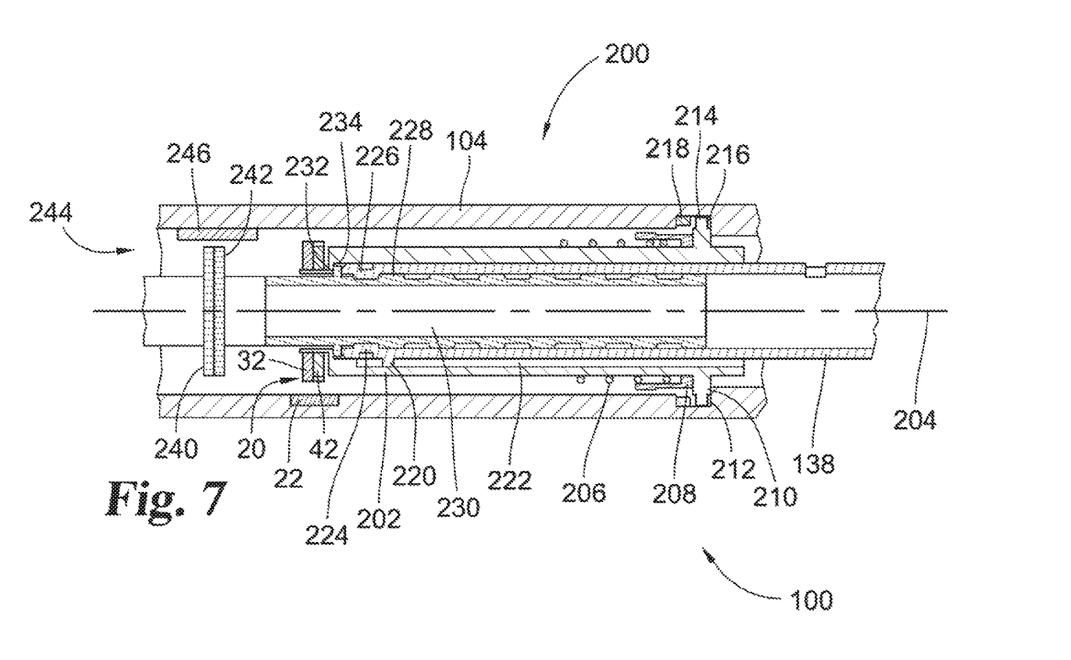
FIG. 7 is a partial cross-sectional view of a medication delivery device equipped with a sensing system.

Referring now to FIGS. 5-7, there is shown a medication delivery device comprising a pen-shaped injection device 100 which is manually handled by a user to selectively set a dose and then to inject that set dose. Injection devices of this general type are well known, and the description herein of device 100 is merely illustrative. The sensing system is shown in use with this described embodiment, but it is readily adaptable for use in variously constructed medication delivery devices for which the relative movement of component members is indicative of the amount of a dose that is set and/or delivered.

Medication injection device 100 includes a casing 102 that supports the internal components of the device. The casing is shown as having a housing 104 and a cartridge retainer 106. Housing 104 holds a mechanical drive mechanism, described hereafter, which is operated to set and deliver a dose of medication. Cartridge retainer 106 holds a cartridge 108 filled with medication to be delivered by the device. Cartridge retainer 106 is detachably mountable to housing 104 via external threading 110 on a protruding collar portion 112 of housing 104 which mates with internal threading 114 on a ring portion 116 at the proximal end of cartridge retainer 106. Suitable detachable mounting elements other than threadings 110 and 114, such as a bayonet fitting, are known in the art and naturally may instead be employed.

Cartridge retainer 106 includes an internal hollow 118 suited to removably receive cartridge 108, thereby allowing a cartridge to be inserted therein, and then removed therefrom when depleted and replaced with a fresh cartridge of similar design. Openings 120 in cartridge retainer 106 allow visibility of the cartridge contents.

Medication cartridge 108 is of conventional design, including a body 122 having an interior reservoir filled with medication which is sealed at one end by a slidable plunger or piston 124 and sealed at the other end by a septum 126 held by a crimp ring 128.

A needle assembly 130 is detachably mountable to an externally threaded distal end 132 of cartridge retainer 106 and pierces the septum 126 when so mounted. The pierced septum through which the needle extends serves as an outlet during dispensing for the medication within the reservoir of body 122, which medication is delivered through the needle assembly 130 by operation of device 100. The cartridge 108 can hold multiple doses of medication, or even a single dose, depending on the purpose of device 100.

Medication injection device 100 is shown in FIG. 5 in its "zero position" at which the device has not been set for delivery of any dose. In FIG. 6, device 100 is arranged after being manipulated to set a dose for delivery.

Medication delivery device 100 is typical of many such devices in including a manually-powered dose delivery mechanism that controls forward advancement of a drive member, generally designated at 134. Drive member 134 advances within the cartridge body 122 to directly engage and advance plunger 124. As shown in FIG. 6, the dose delivery mechanism includes a dose knob 136 connected via a dial sleeve 138 to a mechanical drive assembly within housing 104. When dose knob 136 is turned by a user to set a dose for injection, dose knob 136 and dial sleeve 138 screw out together from housing 104. When a user applies a plunging force on the proximal end 140 of dose knob 136, the resulting forward motion of dose knob 136 and dial sleeve 138 into housing 104 is converted by the mechanical drive assembly into a smaller motion of drive member 134 forward from housing 104 into the interior of cartridge body 122.

Drive member 134 is formed in two pieces including a forward end 142 that directly engages the cartridge plunger 124, and a shaft 144 that axially extends from housing 104. The shaft 144 has external threads 146 and is engaged with the mechanical drive assembly to be driven out from housing 104. Forward end 142 is provided in the form of an enlarged foot that is mounted on shaft 144.

Medication delivery device 100 may include a mechanical drive assembly 200 such as shown in cross section in FIG. 7. A barrel 202 is received within housing 104 and is rotatable relative to the housing about axis 204. Barrel 202 is biased in the proximal direction (to the right in FIG. 7) by a spring 206 and clicker 208. Housing 104 includes a flange 210 which rests against a shoulder 212 of housing 104 when the barrel is in the proximal position. In this position, circumferentially-spaced teeth 214 on barrel 202 are received and move freely within circumferential groove 216 in its interior surface during relative rotation of the barrel and the housing.

Barrel 202 has an alternate position moved distally such that teeth 214 are received by complementary positioned teeth 218 of the housing, locking the barrel against rotation relative to the housing. Alternately, for example, the barrel may be locked by teeth on the barrel bottoming out within the teeth of clicker 208, which is keyed to housing 104.

Dial sleeve 138 is received within barrel 202. A key 220 on dial sleeve 138 is received within longitudinal keyway 222 in barrel 202. This allows the dial sleeve to move axially relative to the barrel, but prevents relative rotation between the two members. The dial sleeve includes tabs 224 and 226 which are engaged with external threads 228 of a drive sleeve 230. Rotation of the dial sleeve relative to the drive sleeve causes the dial sleeve to move axially as tabs 224 and 226 travel along threads 228.

Rotation of the drive sleeve is used to move drive member 134 to deliver a set dose. In one embodiment, for example, drive sleeve 230 is coupled with a drive nut (not shown) that has an internal thread. The internal thread of the drive nut engages the external thread 132 on drive member 134 which is fixed against rotation relative to the housing. In this embodiment, the rotation of the drive sleeve rotates the drive nut, which in turn advances the drive member distally to administer the set dose. It will be appreciated that various other ways are also well known in the art to use the forward movement of the dial sleeve 138 to advance the drive member 134.

The setting of a dose for the foregoing device occurs as follows. Barrel 202 is initially in the proximal position relative to the housing 104 (FIG. 7) and rotates with the teeth 214 spinning freely within circumferential groove 216. Drive sleeve 230 is rotationally fixed by complementary splines (not shown) relative to housing 104. During dose setting, dial sleeve 138 is rotated and spirals up drive sleeve 230. The keyed connection of the barrel and the dial sleeve causes barrel 202 to rotate in unison with dial sleeve 138. However, barrel 202 at the same time is prevented from moving proximally relative to the housing in view of flange 210 being received against shoulder 212. There is therefore relative rotational movement between the housing and the barrel during dose setting which represents the amount of dose set by the medication delivery device, and this movement is detected by sensing system 20.

Targets 32 and 42 are attached to barrel 202. Each of these targets carries an array of teeth. Sensor 22 is coupled with the interior surface of housing 104 such that the teeth of targets 32 and 42 pass through the area sensed by the sensor 22. The sensing system 20 is thereby positioned and operable to detect the relative position of the targets to the sensor, as previously described. The sensor generates outputs that are therefore representative of the relative positions of the barrel and the housing during dose setting.

In order to deliver the set dose, dial sleeve 138 is manually pushed distally. The frictional engagement of the dial sleeve tabs 224 and 226 with the drive sleeve threads 228 initially causes the drive sleeve 230 to advance. An outwardly-extending flange 232 of drive sleeve 230 rests adjacent an interior shoulder 234 of barrel 202 and therefore causes barrel 202 also to move distally. This movement causes the barrel teeth 214 to engage with the housing teeth 218. As a result, further distal movement of drive sleeve 230 and barrel 202 relative to housing 104 is prevented. Further, barrel 202 and keyed dial sleeve 138 are thus also locked against rotation relative to the housing, but the dial sleeve 138 is free to move distally with respect to barrel 202. This distal movement of drive sleeve 230 also disengages the splines fixing the drive sleeve from rotation relative to the housing during dose setting.

At this point, the dial sleeve 138 is free to move distally, but not rotationally, relative to housing 104, and drive sleeve 230 is free to rotate, but not move distally, relative to housing 104. Further force on dial sleeve 138 therefore overcomes the frictional engagement between the tabs 224 and 226 and drive sleeve threads 228, and drive sleeve 230 rotates relative to housing 104. This results in rotation of the drive nut and advancement of the drive member 134 to administer the dose as previously described. Thus, during dose delivery the drive sleeve rotates relative to both the barrel and the housing. This rotation of drive sleeve 230 relative to housing 104 during dose delivery is representative of the amount of dose delivered by the medication delivery device.

As another example, the medication delivery device of FIG. 7 is shown also to comprise a pair of toothed targets 240 and 242 attached to the exterior of the drive sleeve 230. Targets 240 and 242 may be identical to or substantially the same as targets 32 and 42, but that is not required. Sensing system 244 further includes a sensor 246 coupled with housing 104. Rotation of drive sleeve 230 relative to housing 104 causes teeth extending radially outward from targets 240 and 242 to pass through the sensed area of sensor 246. The sensing system is thereby operable to detect the relative positions of drive sleeve 230 and housing 104 during dose delivery. As previously described, relative movement between start and stop positions during dose delivery is directly related to the amount of the dose delivered, and this movement is detected by sensing system 244.

The sensor provides output signals indicative of the characteristic of the sensed parameter corresponding to the relative positions of the members during dose setting and/or delivery. For example, a magneto-resistive sensing system detects a resistance for the sensing element for a given position of the targets relative to the sensor. A processor 248 is operably connected to the sensing system to receive the output from the sensor. The processor may include conventional components such as a controller, power supply, memory, microprocessors, etc. The processor is configured to identify the angular position of the first member relative to the second member based on the received sensor output. The processor 248 is further configured to receive two separate outputs from the sensor corresponding to the start and end relative positions of the first and second members during dose setting and/or dose delivery. The start and end positions are used to determine the amount of the dose set and/or delivered from the received sensor outputs, such as by comparison to a stored table. In one embodiment, the processor is configured to receive sensor outputs from two different sensing systems and to determine both the amount of dose set and the amount of dose delivered from those outputs.

Figure 8:
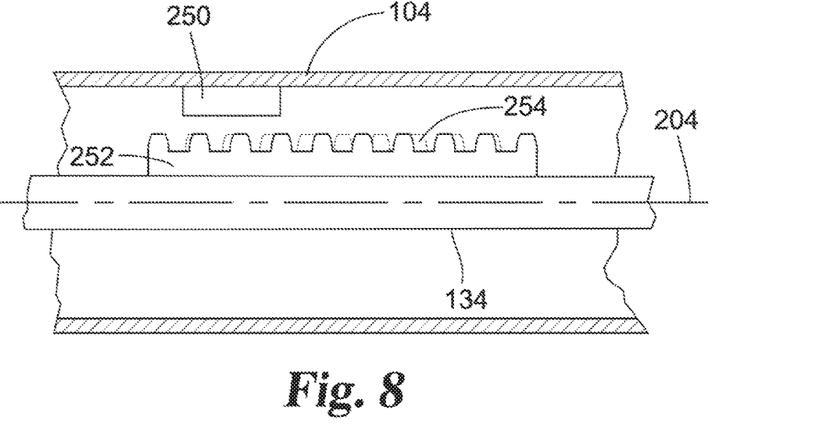
FIG. 8 is a partial schematic view of a sensing system in a medication delivery device.

The sensing system may also be used to determine relative translational movement between two members of a medication delivery device. Shown diagrammatically in FIG. 8 is a portion of a medication delivery device including housing 104 carrying a sensor 250. The device includes a drive member 134 which moves longitudinally relative to housing 104 along axis 204 during dose administration. Coupled with drive member 134 are targets 252 and 254 comprising arrays of teeth. For each array the teeth are substantially identical in shape and uniformly spaced apart. However, the spacing of the teeth for target 252 is different than the spacing of the teeth for target 254.

In the manner previously described, drive member 134 moves axially relative to housing 104 during dose delivery. This axial movement results in different positions of teeth of targets 252 and 254 being received within the sensed area of sensor 250. The one sensor is thereby positioned to detect the effect of the teeth on both targets as they pass through the sensed area. The sensing system is therefore able to detect these different relative positions and to generate outputs representing the relative positions of the members during dose delivery. This information is converted to a value for the dose amount delivered, which may be displayed and recorded by the device. Similarly, the dial sleeve 138 in the embodiment of FIG. 7 moves axially relative to the barrel and the housing during dose delivery and this relative axial movement may be used to determine the amount of dose delivered.

The sensing system of the present invention enables the reliable and accurate determination of an amount of a dose that is set and/or delivered by operation of a medication delivery device. Broadly speaking, the medication delivery device includes first and second members which move relative to one another during dose setting. The members of the medication delivery device have an initial relative position prior to dose setting. This "start position" corresponds to a relative position of the sensor to the targets. The sensing system is used to determine this start position by detecting the sensed parameter for the sensed area. For a magnetoresistive sensor, for example, this initial position may be reflected by a signature resistance that uniquely identifies the position of the teeth within the sensed area. This in turn identifies the position of the targets relative to the sensor, and an output is provided to the processor which records this information.

The sensor thus is operable to sense a characteristic of the sensed parameter representative of a relative position between the first and second members based on the positions of the first and second teeth within the sensed area, and to generate an output correlated to the sensed characteristic. A processor is operably connected to the sensor to receive outputs from the sensor. The processor is configured to identify the position of the first member relative to the second member based on the received sensor output. The processor is further configured to receive two separate outputs from the sensor corresponding to the start and end relative positions of the first and second members for at least one of a dose setting or a dose administration, and to determine the amount of the dose set or administered based on the received outputs.

The medication delivery device may include a plurality of sensing systems as disclosed herein, such as shown in the embodiment of FIG. 7. Different sensing systems may be used to measure dose setting and to measure dose delivery. Multiple sensing systems may also be used for either dose setting or dose delivery to provide redundancy. In a preferred embodiment, the medication delivery device includes multiple sensing systems and the processor is configured to determine the amount of both a set dose and a delivered dose based on corresponding outputs from the sensing systems.

The determined amount of the dose set or administered may be recorded by the medication delivery device and displayed to the patient. An alarm may be provided in the event the dose setting falls outside of an acceptable range. Similarly, an alarm may be provided if the amount of dose delivered does not correspond to the amount set, which may for example be an indication that not all of the set dose was delivered or that the device has otherwise malfunctioned.

Since the sensing system measures relative movement, the particular members with which the sensor and targets are associated are completely reversible. For example, if the two members comprise the housing and the barrel of the medication delivery device, as in FIG. 7, then the sensor may be attached to either member and the targets are then attached to the other member. However, the placement of two sensing system components may be dictated to some extent on other factors, such as the space that is available. Positioning of the sensor on the housing is advantageous to facilitate its connection to a power supply and with electronics used to receive, process, display and record the determined amount of dose that is set and/or delivered. In preferred embodiments, the arrays of teeth operate as passive elements of the sensing system, and it therefore is not required for the targets to be connected to other components of the sensing system. In a typical embodiment for measuring relative rotation, the sensor is coupled with an outer member such as the housing, and the targets are coupled with an opposed, inner member.

It will be appreciated that it is sufficient that the sensor and targets move at least proportionally to the movement of the respective members to which they are coupled. Preferably, the relative movement between the sensor and targets is the same as the relative movement between the first and second members. In a particularly preferred embodiment, the sensor is coupled directly with the first member and the targets are coupled directly with the second member.

While the invention has been illustrated and described in detail in the drawings and foregoing description, the same is to be considered as illustrative and not restrictive in character. All changes, equivalents, and modifications that come within the spirit of the inventions defined by the claims included herein are desired to be protected.

What is claimed is:

1. A sensing system for a medication delivery device comprising:
   a first member of the medication delivery device;
   a second member of the medication delivery device moveable relative to the first member in proportion to at least one of an amount of a dose set and an amount of a dose delivered by operation of the medication delivery device;
   a sensor coupled with the first member, the sensor being operable to detect a sensed parameter within a sensed area of the sensor;
   a first, passive target coupled with the second member and having an array of first teeth positioned to move through the sensed area as the second member moves relative to the first member, the first teeth being substantially identical in shape and uniformly spaced a first distance;
   a second, passive target coupled with the second member and having an array of second teeth positioned to move through the sensed area as the second member moves relative to the first member, the second teeth being substantially identical in shape and uniformly spaced a second distance different from the first distance, the first target being fixed against movement relative to the second target such that the first target and the second target move together at all times,
   the sensor being operable to sense a characteristic of the sensed parameter representative of a relative position between the first and second members based on the combined positions of the first and second teeth within the sensed area, and to generate an output correlated to the sensed characteristic; and
   a processor operably connected to the sensor to receive the output from the sensor, the processor being configured to identify the position of the first member relative to the second member based on the sensor output.

2. The sensing system of claim 1 in which the sensor is operable to generate a first output corresponding to a start position and a second output corresponding to an end position of the first and second members for at least one of a dose setting or a dose delivery, and the processor is further configured to receive the first and second outputs from the sensor and to determine the amount of the dose set and/or delivered from the first and second sensor outputs.

3. The sensing system of claim 1 in which each of the first and second targets has a circular array of outwardly extending teeth.

4. The sensing system of claim 3 in which the first target has one more tooth than the second target.

5. The sensing system of claim 1 in which the sensor comprises a magnetic sensor.

6. The sensing system of claim 5 in which the first and second targets comprise a ferromagnetic material.

7. A medication delivery device comprising:
a first member of the medication delivery device;
a second member of the medication delivery device moveable relative to the first member in proportion to at least one of an amount of a dose set and an amount of a dose delivered by operation of the medication delivery device;
a sensor coupled with the first member, the sensor being operable to detect a sensed parameter within a sensed area of the sensor;
a first, passive target coupled with the second member and having an array of first teeth positioned to move through the sensed area as the second member moves relative to the first member, the first teeth being substantially identical in shape and uniformly spaced a first distance;
a second, passive target coupled with the second member and having an array of second teeth positioned to move through the sensed area as the second member moves relative to the first member, the second teeth being substantially identical in shape and uniformly spaced a second distance different from the first distance, the first target being fixed against movement relative to the second target such that the first target and the second target move together at all times,
the sensor being operable to sense a characteristic of the sensed parameter representative of a relative position between the first and second members based on the combined positions of the first and second teeth within the sensed area, and to generate an output correlated to the sensed characteristic; and
a processor operably connected to the sensor to receive the output from the sensor, the processor being configured to identify the position of the first member relative to the second member based on the sensor output.

8. The medication delivery device of claim 7 in which the sensor is operable to generate a first output corresponding to a start position and a second output corresponding to an end position of the first and second members for at least one of a dose setting or a dose delivery, and the processor is further configured to receive the first and second outputs from the sensor and to determine the amount of the dose set and/or delivered from the first and second sensor outputs.

9. The medication delivery device of claim 7 in which the processor is configured to determine the amount of a set dose.

10. The medication delivery device of claim 7 in which the processor is configured to determine the amount of a delivered dose.

11. The medication delivery device of claim 7 in which the second member and the first and second targets rotate relative to the first member.

12. The medication delivery device of claim 7 in which each of the first and second targets has a circular array of outwardly extending teeth.

13. The medication delivery device of claim 12 in which the first target has one more tooth than the second target.

14. The medication delivery device of claim 7 in which the sensor comprises a magnetic sensor.

15. The medication delivery device of claim 7 which includes a housing, and the sensor is coupled with the housing.

16. The medication delivery device of claim 7, further comprising a medication.

* * * * *